United States Patent [19]
Miller et al.

[11] Patent Number: 5,942,601
[45] Date of Patent: Aug. 24, 1999

[54] PEPTIDE SYNTHESIS WITH SULFONYL PROTECTING GROUPS

[75] Inventors: Stephen C. Miller; Thomas S. Scanlan, both of San Francisco, Calif.

[73] Assignee: The Reagents of The University of California, Oakland, Calif.

[21] Appl. No.: 08/986,148

[22] Filed: Nov. 21, 1997

[51] Int. Cl.[6] .................................. C07K 1/04; C07K 1/06
[52] U.S. Cl. .................... 530/334; 530/337; 562/430; 562/556
[58] Field of Search ...................... 530/334, 337, 530/338; 562/430, 556, 867, 868; 564/87

[56] References Cited

U.S. PATENT DOCUMENTS

| | | | |
|---|---|---|---|
| 4,476,051 | 10/1984 | Fujino et al. | 530/337 |
| 4,582,821 | 4/1986 | Kettner et al. | 514/18 |
| 5,055,451 | 10/1991 | Krantz et al. | 514/19 |
| 5,360,928 | 11/1994 | Carpino et al. | 562/849 |
| 5,545,568 | 8/1996 | Ellman | 436/518 |

FOREIGN PATENT DOCUMENTS

| | | |
|---|---|---|
| 710652 | 5/1996 | European Pat. Off. . |
| 54-84588 | 7/1979 | Japan . |

OTHER PUBLICATIONS

Bowman et al, A Facile Method for the N–Allegation . . . Tetrahedron. Vol. 53, No. 46, pp.15787–15798, Nov.17, 1997.
Chemical Abstracts 82: 66060u, 1975.
Chemical Abstracts 83: 79565h, 1975.
DeRuiter et al, In Vitro Aldase Reductase . . . J. Pharm. Sci. vol. 76, No. 2, pp. 149–152, Feb. 1987.
Fukuyama et al, 2,4–Dinitrobenzenesulfonamides . . . Tet. Lett. vol. 38, No. 33, pp. 5831–5834, Aug. 18, 1997.
Morozov et al, Mechanical Detection of Interaction . . . Analytical Biochem. vol. 201, pp. 68–79, 1992.
Roberts et al, Basics Principles of Organic Chemistry, 2nd ed. Menlo Park: W.A. Benjamin, Inc. pp. 1236–1239, 1977.
Stewart et al, Solid Phase Peptide Synthesis, 2nd ed. Rockford: Pierce Chemical Co. pp. 1–3, 1984.
Wipf et al, Solid–Phase Synthesis of Peptide . . . J. Org. Chem. vol. 62, pp. 1586–1587, Mar. 21, 1997.
Fukuyama, Tohura et al., "2– and 4–Nitrobenzenesulfonamides: Exceptionally Versatile Means for Preparation of Secondary Amines and Protection of Amines.," *Tetrahedron Letters* (1995) vol. 36, No. (36):6373–6374.
Schwesinger, Reinhard, "Extremely Strong, Non–ionic Bases: Synthesis and Applications," *Chimia* (Sep. 1985) vol. 39, No. (9):269–272.
Zervas, Leonidas et al., "New Methods in Peptide Synthesis. I. Tritylsulfenyl and 0–NitroNitrophenylsulfenyl Groups as N–Protecting Groups[1,2]" *J. Amer. Chem. Soc.* (1963) vol. 85:3660–3666.

*Primary Examiner*—Jeffrey E. Russel
*Attorney, Agent, or Firm*—Bozicevic, Field & Francis LLP; Bret Field

[57] ABSTRACT

Methods and compositions are provided for synthesizing peptides with sulfonyl protecting groups. In the subject methods, an sulfonyl group α-amino protected amino acid is contacted with a second amino acid monomeric unit under coupling conditions so that the protected amino acid and second amino acid monomeric unit are joined by a peptide bond. The contacting step may be repeated one more additional times to obtain a peptide of desired length. Also provided are methods of site specific modification using the subject sulfonyl protecting groups. The subject methods find particular use in methods of solid phase peptide synthesis.

14 Claims, No Drawings

PEPTIDE SYNTHESIS WITH SULFONYL PROTECTING GROUPS

TECHNICAL FIELD

The technical field of this invention is peptide synthesis.

BACKGROUND OF THE INVENTION

Peptides (polymers of amino acids) and peptide-like structures can influence a variety of physiological processes, such as the endocrine, neurological, immune and enzymatic processes, with high specificity and potency. As such, peptides are of critical importance to biomedical research and fields related thereto, and have found, or have potential use, in medicine, including the regulation of fertility, the control of pain, the stimulation of growth, the therapy of cancer, cardiovascular applications, treatment of connective tissue diseases, treatment of digestive disorders, treatment of mental illness, treatment of infections by pathogens, and the like.

The demand for peptides is therefore enormous and continues to increase. While natural sources can provide a great variety of peptides, often it is difficult to identify and isolate a particular peptide of interest in useful amounts. Accordingly, peptide synthesis by recombinant DNA or purely chemical means plays an important role.

Modern chemical synthesis of peptides has been summarized as follows: "All modern work in peptide synthesis employs the following approach: the amino group of one amino acid is first stabilized by the introduction of a protecting group R, the carboxyl group is modified so that it is capable of coupling with a second amino acid, the coupling is performed, and finally the group R is removed to produce a finished peptide. The difficulty lies in finding a suitable group R, which can be removed so gently that the peptide is not significantly attacked." Bergmann & Zervas, Berichte der Deutschen Chemischen Gesellschaft (1932) 65: 1192–1201.

For an "R" group to be suitable for use in peptide synthesis, it must satisfy a number of different criteria. It must suppress the nucleophilic reactivity of the α-amino group, either: (a) by draining the α-amino group's electron density away into an appropriate substituent or (b) concealing the group "behind a screen of gross steric hindrance." It should introduce no problems of its own. It should remain firmly in position while needed. It should be removable under conditions that do not adversely affect the rest of the structure being assembled. It should not affect the chiral integrity of nearby asymmetric centers. It should be orthogonal to other protecting groups that are being used.

A number of different "R" groups have been developed for use in chemical peptide synthesis, and include: the alkoxycarbonyl family of amino-protecting groups, such as the Benzyloxycarbonyl (Z) group, the t-Butoxycarbonyl (Boc) group, the 2-(4-Biphenylyl)isopropoxycarbonyl (Bpoc) group, the 9-Fluorenylmethoxycarbonyl(Fmoc) group, the 2,2,2-Trichloroethoxycarbonyl (Troc) group; the triphenylnethyl (trityl, Trt) group; the 2-Nitrophenylsulphenyl (Nps) group; the Dithiasuccinoyl (Dts) group; and the Diphenylphosphinyl (DPP) group.

A significant advance in the field of chemical peptide synthesis occurred in 1963 with Merrifield's development of the technique of solid phase peptide synthesis. Merrifield, J. American Chemical Soc. (1963) 85: 2149–2154. Methods of solid phase peptide synthesis are characterized by the iterative coupling of an α-amino protected amino acid monomer to a solid phase bound amino acid monomeric unit, in which the C-terminal amino acid of the desired peptide product is covalently bound to a solid phase, such as polystyrene. In addition to the α-amino protecting group, any reactive side chain functionalities that may be present on the individual amino acid monomeric units of the growing peptide chain are protected. As such, the "temporary α-amino protecting group must be orthogonal in reactivity to the side chain protecting groups." Since its development, different combinations of α-amino protecting groups and side chain protecting groups have been employed in solid phase peptide synthesis. For example, the Boc group has been employed as the α-amino protecting group in combination with benzyl groups as the side chain protecting groups. Of increasing prevalence is the use of the Fmoc group as the α-amino protecting group in combination with the Boc group, or a similar t-butyl based group, as the side chain protecting group. Although each of the above combinations of protecting groups have been successfully used in the chemical synthesis of a multitude of different properties, no protecting group has been yet been developed that is completely satisfactory.

Accordingly, there is continued interest in the identification of new α-amino protecting groups which are suitable for use in methods of chemical peptide synthesis. Because of its continued growth in popularity in the field of peptide synthesis, of particular interest is the development of new α-amino protecting groups suitable for use in solid phase peptide synthesis.

Relevant Literature

Jones, The Chemical Synthesis of Peptides (Oxford University Press) (1993) provides a review of both solution phase and solid phase peptide synthesis.

SUMMARY OF THE INVENTION

Methods and compositions are provided for peptide synthesis. In the subject methods, a sulfonyl protecting group is used as an α-amino protecting group for at least one amino acid monomer during synthesis. To prepare peptides according to the subject invention, in at least one of the coupling steps in the overall peptide synthesis, an α-amino protected amino acid protected with a sulfonyl protecting group is contacted with a second amino acid monomeric unit under conditions sufficient for coupling to occur through formation of a peptide bond between the α-amino protected amino acid and the second amino acid monomeric unit. The above steps may be repeated one or more additional times with additional α-amino protected amino acids, which may be similarly protected or protected with another α-amino protecting group, to prepare a peptide of desired length. Also provided are methods of N-site specific modification using the subject sulfonyl protecting groups. The subject methods find particular use in solid phase peptide synthesis.

DEFINITIONS

The term "peptide" as used herein refers to any compound produced by amide formation between a carboxyl group of one amino acid and an amino group of another.

The term "oligopeptide" as used herein refers to peptides with fewer than about 10 to 20 residues, i.e. amino acid monomeric units.

The term "polypeptide" as used herein refers to peptides with more than 10 to 20 residues.

The term "protein" as used herein refers to polypeptides of specific sequence of more than about 50 residues.

The term "α-amino protected amino acid" is used herein in its broadest sense to refer to a molecule having an α-amino group in which the N is covalently bonded to moiety which can be selectively removed under appropriate conditions. Therefore, specific examples include o-NBS α-amino protected amino acids, such as amino acids in which the α-amino group is covalently bonded to o-NBS and peptides in which the α-amino group of the N-terminal amino acid monomeric unit is covalently bonded to o-NBS.

The term "second amino acid monomeric unit" refers to an amino acid or amino acid residue in which the α-carboxy group is protected. Thus, second amino acid monomeric units may be amino acids free in solution in which the α-carboxy group is protected, either by a protecting group or through a covalent bond to a polymeric support material, or the N-terminal amino acid residue of a peptide, where the α-carboxy group of the C-terminal residue is protected, either by a protecting group or through covalent linkage to a polymeric support material.

The term "amino acids" as used herein, includes α-amino acids, as well as β-, γ-, δ- and non-naturally occurring amino acids.

DESCRIPTION OF THE SPECIFIC EMBODIMENTS

Methods and compositions are provided for the chemical synthesis of peptides. In the subject methods, a sulfonyl protecting group is used as an α-amino protecting group. To synthesize peptides according to the subject methods, in at least one of the coupling steps of the peptide synthesis protocol a sulfonyl group α-amino protected amino acid is contacted with a second amino acid monomeric unit under coupling conditions, whereby a peptide bond is produced between the α-amino protected amino acid and the second amino acid monomeric unit. The above process may be repeated one or more times to generate a peptide of desired length, where the α-amino protected amino acid monomers may be similarly protected or protected with a different protecting group, e.g. BOC, FMOC and the like. Also provided is a method of N-site specific modification using the subject sulfonyl protecting groups. Of particular interest is the use of the subject methods for solid phase peptide synthesis.

Critical to the subject invention is the use of a sulfonyl protecting group to protect the α-amino acid. By sulfonyl group is meant a group of atoms that comprises a sulfonyl moiety and, generally, is capable of covalently bonding with a primary amine to produce a sulfonamide. Sulfonyl groups that find use in the subject invention typically comprise a sulfonyl group linked to an electron withdrawing group, where the linking moiety may be alkyl or aryl, and will preferably be aryl. Representative sulfonyl protecting groups that find use in the subject invention are shown in Table 1.

TABLE 1

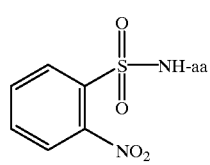

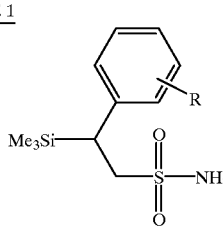

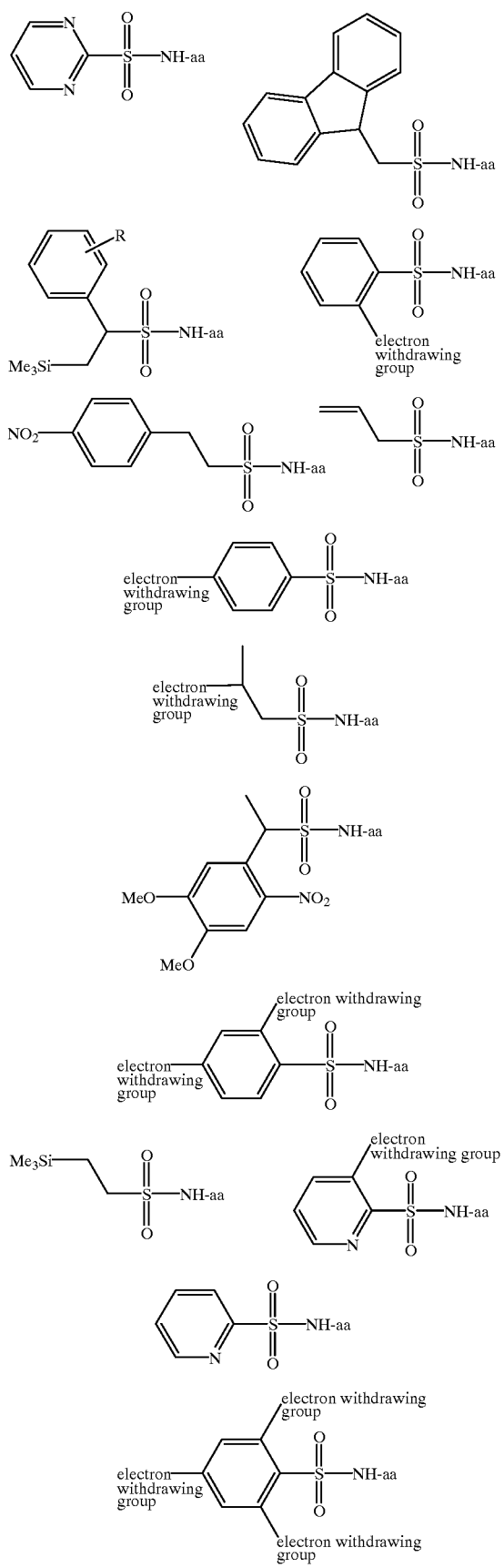

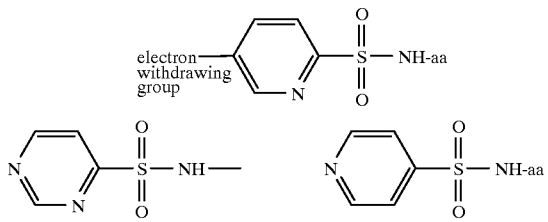

Preferably, the linking group is a nitrobenzene sulfonyl group, the nitro will preferably be ortho or -para to the sulfonyl group. More preferably, o-nitrobenzyl sulfonyl (o-NBS) is the protecting group of the α-amino moeity of the amino acid monomer. In the o-NBS group, a sulfonyl group which may be covalently bonded to the α-amino group of an amino acid is ortho to the nitro group of nitrobenzene. The structure of an o-NBS α-amino protected amino acid which finds use in the preferred embodiments of subject invention may be represented by the generic formula:

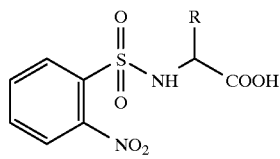

where R is a side chain, such as the side chain found on the naturally occurring amino acids or any one of the variety of non-naturally occurring synthetic amino acids that are known in the art.

In the subject invention, the sulfonyl group is used as an α-amino protecting group for amino acids during peptide synthesis. Amino acids having side chain functional groups may be further side-chain protected, as is known in the art, where conventional side chain protecting groups may be used. Preferably the sulfonyl protecting group is orthogonal in reactivity with respect to the side chain protecting groups. For example: for lysine residues, Boc and Z protecting groups may be employed; for arginine residues, PMC, Pbf and nitro groups may be employed; for aspartic and glutamic acids, benzyl, t-butyl ester, esters of secondary alcohols, e.g. cyclohexyl esters and the like, may be employed; for cysteine, thioacetal groups, TRITYL and t-butyl groups may be employed; for serine, threonine and tyrosine, benzyl and t-butyl groups may be employed; for aspariginine and glutamine, Gln(Mbh) and trityl groups may find use; for histidine, Bom, Bum, and trityl groups may find use; for tryptophan, when side chain protection is indicated, carbamoyl (BOC) protection may find use. The particular reactive side chain protecting group employed will be chosen with respect to a number of parameters, including: overall conditions to which the α-amino acid and peptide produced therefrom are subjected during synthesis, the nature of the amino acid; and the like. In a preferred embodiment of the subject invention in which solid phase synthesis is employed, the reactive side chains of the α-amino protected amino acids will be protected with t-butyl groups.

The α-amino protected amino acids employed in the inventive method may be prepared from commercially available side chain protected amino acids, where sources of such side chain protected amino acids include: Advanced Chemtech, Bachem, Sigma, Novabiochem, and the like; and the appropriate sulfonyl halide, e.g. o-nitrobenzenesulfonyl chloride, which is readily available from Aldrich, Fluka and the like. For example, in preparing the o-NBS α-amino protected amino acids from the above reagents, the reagents will be contacted with each other under conditions sufficient for the α-amino group to become covalently bonded to the sulphonyl group with the concomitant production of HCl, where such conditions are known to those of skill in the art and include: Schotten-Baumann conditions (aq. base (Na$_2$CO$_3$ or NaOH)/dioxane) see e.g. Bodanszky & Bodanszky, Practice of Peptide Synthesis.

In certain embodiments according to the subject invention, i.e. where it is desired to couple the α-amino protected amino acid to a N-substituted amino acid monomeric unit, e.g. an N-allyl substituted amino acid monomeric unit, as described in greater detail below, the α-amino protected amino acid described above may be converted to a highly reactive acid halide, e.g. chloride, where such reactive acid chlorides may be prepared according to methods known to those of skill in the art and described in Feiser & Feiser, Reagents for Organic Synthesis (Wiley), the disclosure of which is herein incorporated by reference.

The second amino acid monomeric unit to which the α-amino protected amino acid covalently bonds through production of a peptide bond is an α-carboxy protected amino acid monomeric unit, where the monomeric unit may be free in solution, at the N-terminal of peptide, where the peptide may be free in solution or stably associated with the surface of, e.g. covalently bonded to, a supporting polymeric material, where preferably the second amino acid monomeric unit (i.e. the α-carboxy protected monomeric unit) will be covalently bound to a solid support, either directly through the α-carboxy group or through an intervening linking chain, e.g. a linking chain of amino acid residues. Where the α-carboxy protected amino acid is free in solution, for example in methods of solution phase peptide synthesis, a variety of α-carboxy groups may be employed, where a plurality of such protecting groups are known in the art and the include: esters, e.g. methyl, ethyl, benzyl, t-butyl, trimethylsilylethyl, phenyl, allyl, phenacyl, and the like. For the preferred solid phase synthesis method embodiments of the subject invention, the α-carboxy group of the second amino acid monomeric unit will be bonded, either directly or through an intervening linking group such as a stretch of one or more amino acid residues, to a polymeric support material, where such polymeric support materials include: cross-linked polystyrene and derivatives thereof; polyamides and derivatives thereof, e.g. Tentagel, PEG, and the like, where preferably the resin will be Tentagel or polystyrene.

In preparing peptides according to the subject invention, the α-amino protected monomer protected with the sulfonyl group will be contacted with the second amino acid monomeric unit in the presence of a coupling agent under conditions sufficient for a peptide bond to form between the α-carboxy group of the α-amino protected amino acid and the unprotected amino group (i.e. primary amine) of the second amino acid monomeric unit. A number of coupling agents are known in the art and may be employed, where such agents include: carbodiimide reagents, such as DCCI, PriN═C═NPri, EtN═C═N(CH$_2$)$_3$NMe$_2$,HCl; isoxazolium reagents, such as those of Woodward and Kemp; acyloxyphosphonium reagents, such as BOP, PyBOP; acyloxyuronium reagents, e.g. TBTU, HBTU, HATU; acid fluorides; and the like. Coupling is carried out in the presence of an appropriate solvent which does not adversely affect the coupling reaction, where suitable solvents include inert solvents such as blocked amides, e.g. DMF, DMA, NMP, sulfoxides, e.g. DMSO; methylene chloride (especially for acid chlorides); and the like. Other components which may be present in the coupling reaction mixture include: HOBt, HOAt, and the like.

Following coupling of the α-amino protected amino acid to the second amino acid monomeric unit, the resultant peptide will be separated from the remaining components of the coupling reaction mixture, where particular components from which the resultant peptide will be separated include reaction byproducts, unreacted amino acid monomers and other reagents, and the like. Separation may be accomplished using any convenient protocol, including one or more washings, and the like.

Following coupling and usually also following washing, at least the sulfonyl N-terminal amino protecting group of the resultant peptide will be removed to yield an unprotected N-terminal amino group or primary amine moiety at the N-terminal residue of the resultant peptide. The sulfonyl protecting group can be removed with thiol nucleophiles, such as thiophenol, mercaptobenzothiazole, 2-mercaptoethanol (particularly where the AA is N-alkylated), thiocresols, and the like. Deprotection will typically take place by contacting the peptide with the thiol nucleophile in the presence of base, e.g. DBU, piperidine, $Et_3N$, DIEM, BEMP, $K_2CO_3$, MTBD, and the like, where bases with a pKa >9, particularly ranging from 11–12, are preferred, in a suitable solvent, where suitable solvents include those described supra suitable for use in the coupling step, and the like, where DMF is preferred.

Where desired, the above steps may be reiterated or repeated one or more additional times, where a new α-amino protected amino acid is contacted with the peptide, where the now unprotected N-terminal amino group (i.e. primary amine) of the peptide of the just added residue of the peptide is now the second amino acid monomeric unit. The α-amino protected amino acid may be similarly protected or protected with another protecting group, such as FMOC or BOC (when its the final residue), where a variety of alternative protecting groups are known to those of skill in the art. Preferably, the protecting group will be o-NBS or FMOC. The above synthesis steps of coupling, washing and deprotecting may be reiterated one or more additional times to produce a peptide of desired length and residue sequence specificity.

At one or more steps in the overall peptide synthesis process, N-subtituent groups may be selectively introduced into the growing peptide chain at the α-amino moiety by the process described in U.S. application Ser. No. 08/761,023, the disclosure of which is herein incorporated by reference. Where this methodology is employed to introduce N-modification, the following summarized steps will be performed prior to removal of the sulfonyl protecting group from the α-amino group of the N-terminal amino acid monomeric unit, as the sulfonyl group serves as the activating group as described in the 08/761,023 application.

Where the sulfonyl group serves as the activating group, to introduce a substituent onto the α-amino moiety, the first step is to deprotonate the α-amino moiety. Deprotonation is accomplished by producing a reaction mixture comprising the peptide to be modified and a molar excess of a strong base, conveniently a non-ionic base having a pKa in the range of about 12 to 15, in combination with a modifying agent in a suitable solvent. Strong bases that find use include: hindered guanidinium bases, MTBD, DBU, DBN, PMG, TMG, low equivalents of BEMP, TBAF, TBD and derivatives, and the like. The modifying agent used to introduce an N-substituent is an electrophilic agent that selectively modifies the deprotonated, sulfonyl group "activated" amide to add the substituent group of interest but will not be strong enough to modify the amide backbone of a polypeptide. Exemplary modifying agents that find use include: alkylating agents such as alkyl nosylates, e.g. methyl nosylate; alkyl halides, e.g. ethyl iodide; allyl bromide; benzyl bromide; propyl iodide; alkyl sulfates, e.g. dimethyl sulfate; Pd-π allyl species; Mitsunobu reactions (Mitsunobu (1981) Synthesis:1), particularly intramolecular, e.g. cyclization reactions; and other agents known in the art. Substituents that may be selectively introduced onto the sulfonyl protected N-terminal amino group by this method include: alkyl, including linear and branched of from 1 to n carbon atoms, where the alkyl group may be substituted with hetero groups, such as nitro-, oxy-, hydroxy-, thio-, carbonyl-, halo-, amino- groups, etc., where when substituted, the substituent is preferably not located on the α-carbon of the alkyl group, where methyl groups are preferred alkyl groups in many embodiments of the invention; alkoxy; aryl, such as benyzl and substituted benzyl groups, e.g. heterosubstituted benzyl; allyl (i.e. hydrocarbons having one or more sites of unsaturation carbon carbon bonds, where allyls may be straight or branched, substituted with one or more hetero groups ); alkylthio; haloalkyl; haloalkoxy; halothio; and the like. Solvents in which the selective N-substitution reaction may be carried out include those solvents listed above as suitable for use in the coupling reaction, where DMF is preferred for alkylation and THF is preferred for Pd-π-allyl species. The above selective N-modification reaction will typically be conducted at about ambient temperature of 20° C. and pressure of one atmosphere. Following selective N-modification as described above, the sulfonyl group can be removed as described above.

Where the above steps are employed to introduce selective α-amino N-substitution at a non-N-terminal residue of the final peptide to be produced, in the next coupling step, use of an sulfonyl protected amino acid chloride, as described above, is preferred for groups larger than methyl, e.g. allyl, while for methyl, HATU & acid fluorides are generally employed.

The final step of the subject methods is to deprotect the protected reactive side chains of the residues of the peptide. In the preferred solid phase peptide synthesis method of the subject invention, the final step of the subject methods further comprises cleavage of the peptide from the polymeric support material. This final deprotection step is typically accomplished by acid treatment by methods known to those of skill in the art, which methods include: HF treatment, TFA treatment, TMSOTf, TMSBr and the like, where TFA treatment is preferred.

All of the above reactions can be carried out over a wide range of temperatures of from about −78° C. to about 150° C., where the temperature at which the reactions are carried out will depend, at least in part, on the solvent used. Depending on the temperature, the time of the reaction can vary between about 5 minutes to about 24 hours.

In the preferred solid phase synthesis embodiment of the subject invention, one or more of the above discussed steps may be automated. A variety of automated peptide synthesis devices are known, commercially available and suitable for use in carrying out the subject methods, where such devices include those devices described U.S. Pat. Nos.: 5,614,608; 5,612,002; 5,593,642; 5,582,801; 5,567,391; 5,565,552; 5,565,173; 5,347,979; 5,362,447; 5,240,680; 5,186,898; 4,816,513; and 4,668,476, the disclosures of which are herein incorporated by reference.

Kits are also provided for carrying out the above described methods. The kits according to the subject invention will at least comprise one or more o-NBS protected amino acids, where the kits may further comprise additional reagents suitable for use in the subject methods, such as coupling reagents, solvents, polymeric support materials and the like. The kits will further comprise instructions for carrying out the above methods with the reagent components of the kit, where the instructions may be present on an enclosed package insert and/or association with the packaging of and/or any containers present in the kit.

The following examples are offered by way of illustration and not by way of limitation.

EXPERIMENTAL

The following examples are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade; and pressure is at or near atmospheric.

A. oNBS Protected Amino Acid Synthesis

The synthesis of oNBS-amino acids was carried out using the standard Schotten-Baumann procedure. Briefly, the amino acid was dissolved in a mixture of dioxane and 1M sodium hydroxide and cooled in an ice bath. o-Nitrobenzenesulfonyl chloride in dioxane was added portionwise with concomitant addition of 1M NaOH. After 2 h, the reaction mixture was worked up in the usual manner.

B. Peptide Synthesis with oNBS-Amino Acids

Peptide synthesis with oNBS-AAs was performed in analogy to routine Fmoc-SPPS; the oNBS-amino acid was activated for coupling with HBTU in 0.4M N-methyl morpholine/DMF, and coupled to Rink Amide MBHA resin for 20 min. After washing the resin with DMF, the oNBS amino-protecting group was removed with a 5% solution of thiophenol in DMF containing an equivalent amount of base. The best results have been obtained with potassium carbonate, which allows virtually complete deprotection in less than 10 minutes. It is essential that the deprotection step be performed under inert atmosphere (e.g., nitrogen or argon) to prevent extensive oxidation of the thiol. The deprotection was conveniently followed by the release of a yellow o-nitrobenzyl chromophore. Following deprotection, the resin was again washed with DMF and coupling of the next amino acid was performed.

C. Synthesis of the Peptide SFLLRN (SEQ ID NO: 01)

In order to demonstrate the viability of this approach, the thrombin receptor activating peptide SFLLRN (SEQ ID NO: 01) was synthesized according the above protocol on an automated peptide synthesizer using the following oNBS-protected amino acids: oNBS-Ser(OtBu)-OH, oNBS-Phe-OH, oNBS-Leu-OH, oNBS-Arg(Pmc)-OH, and oNBS-Asn (Trt)-OH. Analysis of the synthesized peptide by mass spectrometry and HPLC demonstrated that it was identical to SFLLRN (SEQ ID NO: 01) synthesized by Fmoc-SPPS, and was obtained in 85% purity.

D. Selective Alkylation of the Terminal Nitrogen

One great advantage of oNBS-protected amino acids over Fmoc-amino acids is the ability to selectively alkylate the terminal nitrogen. For example, allylation of oNBS-NH-LLRN on Rink Amide MBHA resin was performed with 10 eq allyl methyl carbonate, 10 mol % tris(dibenzylideneacetone)dipalladium(0)-chloroform adduct, 80mol % triphenylphosphine, and 50 eq water in THF for 2 h at rt, to selectively yield the desired allylated peptide in 98% purity by RP-HPLC. Deprotection of the oNBS group was carried out with 10 eq BME/DBU in DMF for 30 min.

Subsequent coupling of Fmoc-amino acids to the highly hindered N-allyl leucine residue has proven problematic, however. The peptide coupling reagent HATU, which is suitable for coupling to N-methyl amino acids, gave ~5% coupling. Acid fluorides, PyBroP, symmetric anhydrides, and other methods proved similarly disappointing.

Fmoc-amino acid chlorides are stable and highly reactive, but tend to be of limited use for solid-phase synthesis due to competing cyclization to the oxazolone. Like Fmoc-amino acids, oNBS-amino acids can be converted to stable amino acid chlorides. However, oNBS-amino acid chlorides cannot form oxazolones, although they will decompose in the presence of base. The relative rates of these processes should determine their usefulness as acylating agents in SPPS. Fmoc-Phe-OH and oNBS-Phe-OH were converted quantitatively to their respective acid chlorides by refluxing in 2M thionyl chloride/dichloromethane for 2 h. Coupling to the N-allyl peptide in dichloromethane with collidine as base gave 16.5% coupling of Fmoc-Phe-Cl versus 68% for oNBS-Phe-Cl. Thus, oNBS-amino acid chlorides are at present the best reagents for coupling to such hindered amino acids on solid support.

It is evident from the above results and discussion that the subject methods have several advantages over previous peptide synthesis methods, particularly solid phase peptide synthesis methods. The subject methods allow for backbone modifications and are better suited for use in difficult reactions, such as coupling of an amino acid to an N-substituted amino group. Furthermore, the o-NBS groups employed in the subject methods are less expensive than other protecting groups such as FMOC. The subject methods are compatible with other methods of peptide synthesis, such as FMOC synthesis, providing for the possibility of using already available FMOC automated peptide synthesis devices and/or using both FMOC and o-NBS protected amino acids together. Furthermore, removal of the o-NBS group during the deprotection step yields a yellow chromophore (an o-nitrobenzene derivative) providing for the possibility of quantitatively monitoring the reaction, e.g. with UV/VIS spectroscopy.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method of solid phase peptide synthesis, said method comprising:

contacting a sulfonyl group α-amino protected first amino acid with a second amino acid monomeric unit stably associated with the surface of a solid polymeric support material in a reaction mixture under conditions sufficient to produce a peptide bond between said sulfonyl group α-amino protected first amino acid and said second amino acid monomeric unit, wherein said second amino acid monomeric unit is side chain protected with a t-butyl protecting group;

separating said solid polymeric support material from the remainder of said reaction mixture;

removing the sulfonyl group from said sulfonyl group α-amino protected first amino acid with a thiol nucleophile in the presence of a base; and optionally repeating said contacting and separating steps one or more additional times;

whereby said peptide is synthesized.

2. The method according to claim 1, wherein said contacting step and separating step are repeated at least one additional time with an additional α-amino protected amino acid.

3. The method according to claim 1, wherein said second amino acid is covalently bonded to said solid polymeric support material.

4. The method according to claim 1, wherein said second amino acid is bonded to said solid polymeric support material through a linking group comprising one or more amino acid residues.

5. A method of solid phase peptide synthesis, said method comprising:

contacting a nitrobenzene sulfonyl α-amino protected amino acid with a second amino acid monomeric unit stably associated with the surface of a solid polymeric support material in a reaction mixture under conditions sufficient to produce a peptide bond between said nitrobenzene sulfonyl α-amino protected amino acid and said second amino acid monomeric unit, wherein said second amino acid monomeric unit is side chain protected with a t-butyl protecting group;

separating said solid polymeric support material from the remainder of said reaction mixture;

removing the nitrobenzene sulfonyl group from said nitrobenzene sulfonyl α-amino protected first amino acid with a thiol nucleophile in the presence of a base; and optionally repeating said contacting and separating steps one or more additional times;

whereby said peptide is synthesized.

6. The method according to claim 5, wherein said second amino acid monomeric unit is covalently bonded to said polymeric support material.

7. The method according to claim 5, wherein said second amino acid monomeric unit is bonded to said polymeric support material through a linking group comprising one more amino acid residues.

8. The method according to claim 5, wherein said method further comprises separating said peptide from said polymeric support material.

9. The method according to claim 5, wherein said nitrobenzene sulfonyl α-amino protected amino acid comprises a reactive α-carboxyl group.

10. The method according to claim 9, wherein said nitrobenzene sulfonyl α-amino protected amino acid is an acid chloride.

11. A method of solid phase peptide synthesis, said method comprising:

contacting an o-nitrobenzene sulfonyl α-amino protected amino acid comprising a reactive α-carboxyl group with a second amino acid monomeric unit stably associated with the surface of a solid polymeric support material in a reaction mixture under conditions sufficient to produce a peptide bond between said o-nitrobenzene sulfonyl α-amino protected amino acid and said second amino acid monomeric unit, wherein said second amino acid monomeric unit is side chain protected with a t-butyl protecting group;

separating said solid polymeric support material from the remainder of said reaction mixture;

removing the o-nitrobenzene sulfonyl group from said o-nitrobenzene sulfonyl α-amino protected amino acid with a thiol nucleophile in the presence of a base; and optionally repeating said contacting and separating steps one or more additional times to produce a peptide of desired length; and separating said peptide of desired length from said solid polymeric support material;

whereby said peptide is synthesized.

12. In a method of solid phase peptide synthesis in which t-butyl groups are employed as side chain protecting groups, the improvement comprising:

using a sulfonyl comprising group as an α-amino protecting group.

13. A kit for use in solid phase peptide synthesis, said kit comprising:

at least one sulfonyl group α-amino protected amino acid;

a thionucleophile; and a base.

14. The kit according to claim 13, wherein said kit further comprises a polymeric support material.

* * * * *

SEQUENCE LISTING

<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: synthetic peptide -continued

```
<400> SEQUENCE: 1

Ser Phe Leu Leu Arg Asn
    1               5
```